US009255934B2

(12) United States Patent
Krizman et al.

(10) Patent No.: US 9,255,934 B2
(45) Date of Patent: Feb. 9, 2016

(54) SRM/MRM ASSAY FOR THE INSULIN RECEPTOR PROTEIN

(71) Applicant: Expression Pathology, Inc., Rockville, MD (US)

(72) Inventors: David B. Krizman, Gaithersburg, MD (US); Wei-Li Liao, Herndon, VA (US); Sheeno Thyparambil, Frederick, MD (US); Todd Hembrough, Gaithersburg, MD (US)

(73) Assignee: Expression Pathology, Inc., Rockville, MD (US)

( * ) Notice: Subject to any disclaimer, the term of this patent is extended or adjusted under 35 U.S.C. 154(b) by 0 days.

(21) Appl. No.: 14/328,209

(22) Filed: Jul. 10, 2014

(65) Prior Publication Data
US 2014/0322245 A1 Oct. 30, 2014

Related U.S. Application Data

(63) Continuation of application No. PCT/US2013/021074, filed on Jan. 10, 2013.

(60) Provisional application No. 61/585,202, filed on Jan. 10, 2012.

(51) Int. Cl.
| G01N 33/53 | (2006.01) |
| G01N 33/74 | (2006.01) |
| C12Q 1/37 | (2006.01) |
| G01N 33/574 | (2006.01) |
| G01N 33/68 | (2006.01) |
| H01J 49/00 | (2006.01) |
| H01J 49/26 | (2006.01) |

(52) U.S. Cl.
CPC ........ G01N 33/74 (2013.01); C12Q 1/37 (2013.01); G01N 33/57488 (2013.01); G01N 33/6848 (2013.01); H01J 49/0031 (2013.01); G01N 2333/72 (2013.01); H01J 49/004 (2013.01); H01J 49/0027 (2013.01); H01J 49/26 (2013.01)

(58) Field of Classification Search
None
See application file for complete search history.

(56) References Cited

U.S. PATENT DOCUMENTS

| 7,473,532 | B2 * | 1/2009 | Darfler et al. ............... 435/7.2 |
| 2004/0214338 | A1 * | 10/2004 | Borchers ........................ 436/86 |
| 2005/0037389 | A1 | 2/2005 | Santin |
| 2007/0059784 | A1 | 3/2007 | Ebina et al. |
| 2010/0267927 | A1 | 10/2010 | Garrett et al. |
| 2011/0028344 | A1 | 2/2011 | Krizman et al. |
| 2011/0105337 | A1 | 5/2011 | Krizman |
| 2011/0275644 | A1 | 11/2011 | Buck et al. |

FOREIGN PATENT DOCUMENTS

WO  WO-2011046871 A1  4/2011

OTHER PUBLICATIONS

Belfiore et al. (Current Pharmaceutical Design 2007, vol. 13, p. 671-686).*
International Search Report and Written Opinion in International application No. PCT/US13/21074, mailing date May 28, 2013, 17 pages.

* cited by examiner

Primary Examiner — Jacob Cheu
(74) Attorney, Agent, or Firm — Perkins Coie LLP

(57) ABSTRACT

Specific peptides, and derived ionization characteristics of the peptides, from the Insulin Receptor protein (IR), and its isoforms IR-A and IR-B, that are particularly advantageous for quantifying the IR protein, IR-A isoform and/or IR-B isoform, directly in biological samples that have been fixed in formalin by the method of Selected Reaction Monitoring (SRM) mass spectrometry, or what can also be termed as Multiple Reaction Monitoring (MRM) mass spectrometry. Such biological samples are chemically preserved and fixed and are selected from tissues and cells treated with formaldehyde containing agents/fixatives including formalin-fixed tissue/cells, formalin-fixed/paraffin embedded (FFPE) tissue/cells, FFPE tissue blocks and cells from those blocks, and tissue culture cells that have been formalin fixed and or paraffin embedded. A protein sample is prepared from said biological sample using the Liquid Tissue™ reagents and protocol and the IR protein, and IR-A and/or IR-B isoforms, is quantitated in the Liquid Tissue™ sample by the method of SRM/MRM mass spectrometry by quantitating in the protein sample at least one or more of the peptides described. These peptides can be quantitated if they reside in a modified or an unmodified form. An example of a modified form of an IR peptide is phosphorylation of a tyrosine, threonine, serine, and/or other amino acid residues within the peptide sequence.

18 Claims, No Drawings

SRM/MRM ASSAY FOR THE INSULIN RECEPTOR PROTEIN

This application is a continuation of International Application No. PCT/US13/21074, filed Jan. 10, 2013, which claims the benefit of U.S. Provisional Application No. 61/585,202, filed Jan. 10, 2012, each of which are entitled "SRM/MRM Assay for the Insulin Receptor Protein," the contents of each of which are hereby incorporated by referenced in their entireties This application also contains a sequence listing submitted electronically via EFS-web, which serves as both the paper copy and the computer readable form (CRF) and consists of a file entitled "001152_8029_US01_SEQ_LISTING", which was created on Jul. 10, 2014, which is 1,320 bytes in size, and which is also incorporated by reference in its entirety.

INTRODUCTION

The proliferative actions of insulin-like growth factors I and II (IGF-I and IGF-II respectively) are thought to be largely due to their activation of the insulin-like growth factor receptor (IGF-IR). IGF-II, however, can also bind to and activate the embryonal isoform of the insulin receptor (IR-A) found in numerous cancers. See e.g., Denley et al., Endocrinology 147(2):1029-1036 (2006). In response to insulin-like growth factor-II (IGF-II), IR-A protein signals a proliferative, anti-apoptotic signal. In addition, IGF-II itself can be secreted by tumors to establish an autocrine proliferative loop in which it binds its receptor (IGF-1R), and the IR-A receptor if present. One consequence of IGF-II signaling via IR-A is induction of IR-A mediates resistance to IGF-IR inhibitory drugs, including those that are currently in development.

Specific peptides derived from subsequences of the Insulin Receptor protein (referred to as IR) suitable for determining the level and type of insulin receptor isoforms (IR-A and IR-B) present in a sample are provided. The peptide sequence and fragmentation/transition ions for each peptide are particularly useful in a mass spectrometry-based Selected Reaction Monitoring (SRM) assay(s), which can also be referred to as Multiple Reaction Monitoring (MRM) assay(s). Such assays are referred to herein as SRM/MRM assay(s). The use of peptides for quantitative SRM/MRM analysis of the IR protein(s), and quantitative analysis of different isoforms of the IR protein (e.g., IR-A and IR-B), is described.

This SRM/MRM assay can be used to measure relative or absolute quantitative levels of one or more of the specific peptides from the IR protein. This provides a means of measuring not only the amount of total IR protein(s), but also the amount(s) of the IR-A and IR-B isoforms, in a given protein preparation obtained from a biological sample by mass spectrometry.

More specifically, the SRM/MRM assay can measure these peptides directly in complex protein lysate samples prepared from cells procured from patient tissue samples, such as formalin-fixed cancer patient tissue. Methods of preparing protein samples from formalin fixed tissue are described in U.S. Pat. No. 7,473,532, the contents of which are hereby incorporated by reference in their entirety. The methods described in U.S. Pat. No. 7,473,532 may conveniently be carried out using Liquid Tissue™ reagents and protocols available from OncoPlexDx (formerly Expression Pathology Inc. (Rockville, Md.)).

The most widely and advantageously available form of tissues from cancer patients tissue is formalin fixed, paraffin embedded tissue. Formaldehyde/formalin fixation of surgically removed tissue is by far the most common method of preserving cancer tissue samples worldwide and is the accepted convention for standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of IR protein(s), in addition to accurate and precise quantitative levels of the IR-A and IR-B isoforms, within specific tissue samples (e.g., cancer tissue sample) of a patient or subject from whom the tissue (biological sample) was collected and preserved. This not only provides diagnostic information about the cancer, but also permits a physician or other medical professional to determine appropriate therapy for the patient. For example, such an assay can be designed to diagnose the stage or degree of a cancer and determine a therapeutic agent to which a patient is most likely to respond. Such an assay that provides diagnostically and therapeutically important information about levels of protein expression in a diseased tissue or other patient sample is termed a companion diagnostic assay.

SUMMARY

The assays described herein measure relative or absolute levels of specific unmodified peptides from the IR protein and also can measure absolute or relative levels of specific modified peptides from the IR protein. Examples of modifications include phosphorylated amino acid residues (e.g. phosphotyrosine, phosphoserine and phosphothreonine) and glycosylated amino acid residues (e.g. glycosylated asparagine residues) that are present on the peptides.

Relative quantitative levels of the IR protein, IR-A isoform and/or IR-B isoform, are determined by the SRM/MRM methodology for example by comparing SRM/MRM signature peak areas (e.g., signature peak area or integrated fragment ion intensity) of an individual IR peptide in different samples (e.g., a control sample and a sample prepared from a patient's or subject's tissue). Alternatively, it is possible to compare multiple SRM/MRM signature peak areas for multiple IR signature peptides, where each peptide has its own specific SRM/MRM signature peak to determine the relative IR protein, IR-A isoform and/or IR-B isoform content in one biological sample with the IR protein, and IR protein, IR-A isoform and/or IR-B isoform content in one or more additional or different biological samples. In this way, the amount of a particular peptide, or peptides, from the IR protein and therefore the amount of the IR protein, and IR-A and/or IR-B isoforms, is determined relative to the same IR peptide, or peptides, across 2 or more biological samples under the same experimental conditions. In addition, relative quantitation can be determined for a given peptide, or peptides, from the IR protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the IR protein, and therefore the amount of the IR protein, IR-A isoform and/or IR-B isoform, is determined relative one to another within the same sample. These approaches permit quantitation of an individual peptide, or peptides, from the IR protein to the amount of another peptide, or peptides, between samples and within samples wherein the amounts as determined by peak area are relative one to another, regardless of the absolute weight to volume or weight to weight amounts of the IR peptide in the protein preparation from the biological sample. Relative quantitative data about individual signature peak areas between different samples are normalized to the amount of protein analyzed per sample. Relative quantitation can be performed across many peptides from multiple proteins and the IR protein simultaneously in a single sample and/or across many samples to gain insight into relative protein amounts, one peptide/protein with respect to other peptides/proteins.

Absolute quantitative levels of the IR protein, IR-A isoform and/or IR-B isoform, are determined by, for example, the SRM/MRM methodology whereby the SRM/MRM signature peak area of an individual peptide from the IR protein in one biological sample is compared to the SRM/MRM signature peak area of a known amount of an exogenously added "spiked" internal standard. In one embodiment, the internal standard is a synthetic version of the same exact IR peptide that contains one or more amino acid residues labeled with one or more heavy isotopes. Suitable isotope labeled internal standards are synthesized so that when analyzed by mass spectrometry each standard generates a predictable and consistent SRM/MRM signature peak that is different and distinct from the native IR peptide signature peak and which can be used as a comparator peak. Thus when the internal standard is spiked in a known amount into a protein or peptide preparation from a biological sample and analyzed by mass spectrometry, the SRM/MRM signature peak area of the native peptide from the sample can be compared to the SRM/MRM signature peak area of the internal standard peptide. This numerical comparison provides either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived or subject-derived tissue, such as formalin fixed tissue, and to aid in determining which therapeutic agent would be most advantageous for use in treating that patient or subject. Cancer tissue that is removed from a patient or subject, either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient's or subject's tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer.

Assays of protein levels (e.g., IR, IR-A or IR-B) can also be used to diagnose the stage of cancer in a patient or subject diagnosed with cancer by employing one or more (i.e., one, two, three or four) of the IR protein, IR-A isoform and/or IR-B isoform levels or the IR-A/IR-B ratio. Where the ratio is employed the ratio may be IR-A/IR-B ratio may be greater than 0.10, 0.05, 0.07, 0.1, 0.2, 0.4, 0.5, 0.75, 1.0 1.5, 2.0, 2.25, 2.5, 4, 5, 7.5 or 10 depending on the tissue and cancer.

Insulin receptor (IR) over-expression is common in cancers, with expression of the embryonic version of the IR protein, the A isoform (IR-A, lacking exon 11) predominating over the B isoform (IR-B with exon 11). The assays described herein are capable of determining/detecting the presence and amount of the IR-A isoform present in the biological sample. The implication of the presence of IR-A is that this specific isoform is capable of binding the insulin-like growth factor-II at a higher affinity than the IR-B isoform, and thus imparting resistance to IGF-1R-mediated therapy.

Embodiments set forth herein include methods of determining the resistance (or conversely susceptibility) of a cancer to an antagonist of IGF-1R. Such embodiments comprise determining the presence or level of IR, IR-A, or the ratio of IR-A to IR-B in a cancer tissue; wherein the presence of IR, IRA or an increased ratio of IR-A to IR-B relative to control tissue is indicative of a resistance of said cancer to said antagonist of IGF-IR. One embodiment comprises determining the presence or level of IR-A, or the ratio of IR-A to IR-B in a cancer tissue; wherein the presence of IRA or an increased ratio of IR-A to IR-B relative to control tissue is indicative of a resistance of said cancer to said antagonist of IGF-IR. Where the ratio of IR-A/IR-B is employed, the ratio indicating resistance to IGF-1R may be greater than 0.10, 0.05, 0.07, 0.1, 0.2, 0.4, 0.5, 0.75, 1.0 1.5, 2.0, 2.25, 2.5, 4, 5, 7.5 or 10 depending on the tissue and cancer.

Methods of determining the resistance (or susceptibility) of a cancer to an antagonist of IGF-1R may be extended to the selection of a therapy and/or therapeutic for the treatment of a patient or subject suffering from the cancer. In some embodiments, where the cancer has IR-A or a sufficiently high IR-A/IR-B ratio to indicate resistance to IGF-1R antagonists, the therapy and/or therapeutic employed would omit the use of IGF-1R antagonists.

In methods of determining the resistance (or conversely the susceptibility) of a cancer to an antagonist of IGF-1R, the antagonist of IGF-1R is a protein or peptide (poly peptide) that binds to the IGF-1R. In one embodiment the protein or peptide (polypeptide) comprises: a human antibody; b. a humanized antibody; c. a chimeric antibody; d. a monoclonal antibody; e. a monospecific antibody; f. a recombinant antibody; g. an antigen-binding antibody fragment; h. a single chain antibody; i. a diabody; j. a triabody; k. a tetrabody; l. a Fab fragment; m. a F(ab')$_2$ fragment; n. a domain antibody; o. an IgD antibody; p. an IgE antibody; q. an IgM antibody; r. an IgG1 antibody; s. an IgG2 antibody; t. an IgG3 antibody; or u. an IgG4 antibody. In still other embodiments the protein is an antibody or a monoclonal antibody. In one embodiment the antibody is selected from any one, or a combination of any two, or all three of R1507 (Roche), OSI-906 (OSI Pharmaceuticals) and/or figitumumab. In another embodiment, the antagonist of IGF-1R is a tyrosine kinase inhibitor.

Levels or amounts of proteins or peptides can be defined as the quantity expressed in moles, mass or weight of a protein or peptide determined by the SRM/MRM assay. The level or amount may be normalized to the total level or amount of protein or another component in the lysate analyzed (e.g., expressed in micromoles/microgram of protein or micrograms/microgram of protein). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed. Information regarding the IR protein, and the IR-A and or IR-B isoforms, can thus be used to aid in determining stage or grade of a cancer by correlating the level of the IR protein, the IR-A and/or IR-B isoforms, or fragment peptides of the IR protein with levels observed in normal tissues. Once the stage and/or grade, and/or IR protein, and the IR-A and/or IR-B isoform expression characteristics of the cancer has been determined, that information can be matched to a list of therapeutic agents (chemical and biological) developed to specifically treat cancer tissue that is characterized by, for example, abnormal expression of the protein or protein(s) (e.g., IR and IR-A and/or IR-B isoforms) that were assayed. Matching information from an IR, and IR-A and/or IR-B isoform, protein assay to a list of therapeutic agents that specifically targets, for example, the IR protein, and IR-A and/or IR-B isoforms, or cells/tissue expressing the IR protein and the IR-A and/or IR-B isoforms defines what has been termed a personalized medicine approach to treating disease. The assay methods described herein form the foundation of a personalized medicine approach by using analysis of proteins from the patient's or subject's own tissue as a source for diagnostic and treatment decisions.

A method is provided for measuring the level of the Insulin Receptor (IR) protein, and/or its isoforms, IR-A and/or IR-B, in a biological sample, comprising detecting and/or quantifying the amount of one or more modified or unmodified IR fragment peptides in a protein digest prepared from said biological sample using mass spectrometry; and calculating the level of modified or unmodified IR, IR-A isoform and/or IR-B isoform, protein in the sample; and where the amount is a relative amount or an absolute amount.

The method may further comprise the step of fractionating the protein digest prior to detecting and/or quantifying the amount of one or more modified or unmodified IR fragment peptides. The fractionating step may be, for example, gel electrophoresis, liquid chromatography, capillary electrophoresis, nano-reversed phase liquid chromatography, high performance liquid chromatography, or reverse phase high performance liquid chromatography. The protein digest of the biological sample may be prepared by the Liquid Tissue™ protocol. In a particular embodiment, the protein digest comprises a protease digest, for example, a trypsin digest.

In these embodiments, the mass spectrometry may comprise tandem mass spectrometry, ion trap mass spectrometry, triple quadrupole mass spectrometry, MALDI-TOF mass spectrometry, MALDI mass spectrometry, and/or time of flight mass spectrometry. The mode of mass spectrometry used may be, for example, Selected Reaction Monitoring (SRM), Multiple Reaction Monitoring (MRM), and/or multiple Selected Reaction Monitoring (mSRM), or any combination thereof.

In these embodiments, the IR fragment peptide may comprise an amino acid sequence as set forth in SEQ ID NO:1, SEQ ID NO:2, SEQ ID NO:3, SEQ ID NO:4, and SEQ ID NO:5.

In any of these embodiments, the biological sample may be a blood sample, a urine sample, a serum sample, an ascites sample, a sputum sample, lymphatic fluid, a saliva sample, a cell, or a solid tissue. The tissue may be formalin fixed tissue and/or may be paraffin embedded tissue. The tissue may be obtained from a tumor, for example, a primary tumor or a secondary tumor.

In any of these embodiments the method may further comprise quantifying a modified or unmodified IR fragment peptide. Quantifying the IR fragment peptide may comprise comparing an amount of one or more IR fragment peptides comprising an amino acid sequence of about 8 to about 45 amino acid residues of IR as shown in SEQ ID NO:1, SEQ ID NO:2, SEQ ID NO:3, SEQ ID NO:4, or SEQ ID NO:5 in one biological sample to the amount of the same IR fragment peptide in a different and separate biological sample. Quantifying one or more IR fragment peptides may comprise determining the amount of the each of the IR fragment peptides in a biological sample by comparison to an added internal standard peptide of known amount, where each of the IR fragment peptides in the biological sample is compared to an internal standard peptide having the same amino acid sequence. The internal standard peptide may be an isotopically labeled peptide. The isotopically labeled internal standard peptide may contain one or more heavy stable isotopes selected from $^{18}O$, $^{17}O$, $^{34}S$, $^{15}N$, $^{13}C$, $^{2}H$ or combinations thereof.

In any of these embodiments, detecting and/or quantifying the amount of one or more modified or unmodified IR fragment peptides in the protein digest may indicate the presence of modified or unmodified IR protein, IR-A and/or IR-B, and an association with cancer in a patient or subject. The method may further comprise correlating the results of the detecting and/or quantifying the amount of one or more modified or unmodified IR fragment peptides, or the amount of said IR protein, IR-A isoform and/or IR-B isoform, to the diagnostic stage/grade/status of the cancer. Correlating the results of the detecting and/or quantifying the amount of one or more modified or unmodified IR fragment peptides, or the amount of said IR protein, IR-A isoform and/or IR-B isoform, to the diagnostic stage/grade/status of the cancer may be combined with detecting and/or quantifying the amount of other proteins or peptides from other proteins in a multiplex format to provide additional information about the diagnostic stage/grade/status of the cancer.

The method of any one of the embodiments above may further comprise selecting, for a patient or subject from which the biological sample was obtained, a treatment based on the presence, absence, or amount of one or more IR fragment peptides or the amount of IR protein, IR-A isoform and/or IR-B isoform.

The method of any one of the embodiments above may further comprise administering to a patient or patient from which the biological sample was obtained a therapeutically effective amount of a therapeutic agent, where the therapeutic agent and/or amount of the therapeutic agent administered is based upon the amount of one or more modified or unmodified IR fragment peptides or the amount of IR protein, IR-A isoform and/or IR-B isoform. The treatment or the therapeutic agent may be directed to cancer cells expressing IR protein, IR-A isoform and/or IR-B isoform.

In any of the embodiments above, the biological sample may be formalin fixed tumor tissue that has been processed for quantifying the amount of one or more modified or unmodified IR fragment peptides employing the Liquid Tissue™ protocol and reagents.

In the method of any of the embodiments above the one or more modified or unmodified IR fragment peptides may be one or more of the peptides in Table 1. The method may comprise quantifying the amount of one, two, three, four or five of the peptides in Table 2.

Also provided are compositions comprising one or more, two or more, three or more, or four or more of the peptides in Table 1 and/or antibodies thereto, and compositions comprising one or more, two or more, three or more, or four or more of the peptides of Table 2 or antibodies thereto.

Methods are provided for determining the resistance of a cancer to an antagonist of IGF-1R, comprising determining the presence or level of IR-A, or the ratio of IR-A to IR-B in a cancer tissue; where the presence of IRA or an increased ratio of IR-A to IR-B relative to control tissue is indicative of a resistance of said cancer to said antagonist of IFG-IR. The antagonist of IGF-1R may comprise a protein or peptide that binds to the IGF-1R. The protein or peptide may be, for example, an antibody, for example, a human antibody; humanized antibody; chimeric antibody; monoclonal antibody; monospecific antibody; recombinant antibody; antigen-binding antibody fragment; single chain antibody; diabody; triabody; tetrabody; Fab fragment; F(ab')2 fragment; domain antibody; IgD antibody; IgE antibody; IgM antibody; IgG1 antibody; IgG2 antibody; IgG3 antibody; or IgG4 antibody. The antibody may be selected from R1507, OSI-906 or figitumuab.

DETAILED DESCRIPTION

In principle, any predicted peptide derived from the IR protein, prepared for example by digesting with a protease of known specificity (e.g. trypsin or endoproteinase Lys-C), can be used as a surrogate reporter to determine the abundance of IR protein, and IR-A and/or IR-B isoforms of the IR protein, in a sample using a mass spectrometry-based SRM/MRM assay. Similarly, any predicted peptide sequence containing an amino acid residue at a site that is known to be potentially modified in the IR protein also can be used to assay the extent of modification of IR protein, and IR-A and/or IR-B isoforms, in a sample.

IR fragment peptides may be generated by a variety of ways including using the Liquid Tissue™ protocol described, for example, in U.S. Pat. No. 7,473,532. The Liquid Tissue™ protocol and reagents produce peptide samples suitable for mass spectroscopic analysis from formalin fixed paraffin embedded tissue by proteolytic digestion of the proteins in the tissue/biological sample. Suitable reagents and protocols also are commercially available from OncoPlexDx (formerly Expression Pathology Inc., Rockville, Md.).

In the Liquid Tissue™ protocol the tissue/biological is heated in a buffer for an extended period of time (e.g., from about 80° C. to about 100° C. for a period of time from about 10 minutes to about 4 hours, for example, for about 60 or about 90 minutes to about 4, 6, or 8 hours) to reverse or release protein cross-linking. The buffer employed is a neutral buffer, (e.g., a Tris-based buffer, or a buffer containing a detergent) and advantageously is a buffer that does not interfere with mass spectrometric analysis. Following heat treatment, the tissue/biological sample is treated with one or more proteases, including but not limited to trypsin, chymotrypsin, pepsin, and endoproteinase Lys-C for a time sufficient to disrupt the tissue and cellular structure of said biological sample and to liquefy the sample. Exemplary conditions for the protease treatment are from about 30 minutes or about 60 minutes to about 6 hours, about 12 hours, or about 24 hours at a temperature from about 37° C. to about 65° C. Advantageously, endoproteases, and particularly combinations of two or three endoproteases, used either simultaneously or sequentially, are employed to liquefy the sample. For example, suitable combinations of proteases can include, but are not limited to, combinations of trypsin, endoproteinase Lys-C and chemotrypsin, such as trypsin and endoproteinase Lys-C. The result of the heating and proteolysis is a liquid, soluble, dilutable biomolecule lysate. Advantageously, this liquid lysate is free of solid or particulate matter that can be separated from the lysate by centrifugation.

Once lysates are prepared, peptides in the samples may be subject to a variety of techniques that facilitate their analysis and measurement by mass spectrometry. In one embodiment, the peptides may be separated by an affinity technique, such as for example immunologically-based purification (e.g., immunoaffinity chromatography), chromatography on ion selective media, or if the peptides are modified, by separation using appropriate media, such as lectins for separation of carbohydrate modified peptides. In one embodiment, the SISCAPA method, which employs immunological separation of peptides prior to mass spectrometric analysis is employed. The SISCAPA technique is described, for example, in U.S. Pat. No. 7,632,686. In other embodiments, lectin affinity methods (e.g., affinity purification and/or chromatography may be used to separate peptides from a lysate prior to analysis by mass spectrometry. Methods for separation of groups of peptides, including lectin-based methods, are described, for example, in Geng et al., J. Chromatography B, 752:293-306 (2001). Immunoaffinity chromatography techniques, lectin affinity techniques and other forms of affinity separation and/or chromatography (e.g., reverse phase, size based separation, ion exchange) may be used in any suitable combination to facilitate the analysis of peptides by mass spectrometry.

Surprisingly, it was found that many potential peptide sequences from the IR protein are unsuitable or ineffective for use in mass spectrometry-based SRM/MRM assays for reasons that are not immediately evident. In particular it was found that many tryptic peptides from the IR protein could not be detected efficiently or at all in a Liquid Tissue lysate from formalin fixed, paraffin embedded tissue. As it was not possible to predict the most suitable peptides for MRM/SRM assay, it was necessary to experimentally identify modified and unmodified peptides in actual Liquid Tissue™ lysates to develop a reliable and accurate SRM/MRM assay for the IR protein, and IR-A and/or IR-B isoforms of the protein. While not wishing to be bound by any theory, it is believed that some peptides might, for example, be difficult to detect by mass spectrometry because they do not ionize well or produce fragments that are not distinct from those generated from other proteins. Peptides may also fail to resolve well in separation (e.g., liquid chromatography), or may adhere to glass or plastic ware, which leads to erroneous results in the assay. Accordingly, those peptides from the IR protein (and its A and B isoforms) that can be detected in a Liquid Tissue lysate (e.g., the peptides in Tables 1 and 2) prepared from a formalin fixed tissue sample are the peptides for which SRM/MRM assays can be employed in an IR protein SRM/MRM assay.

In one embodiment the protease employed in the simultaneous preparation of fragments of IR-A and IR-B in a single sample will be trypsin. In another embodiment the protease employed will be Lys-C. In still other embodiments, the protease employed will be a combinations of trypsin and LysC.

IR peptides found in various embodiments of this disclosure (e.g., Tables 1 and/or 2, below) were derived from the IR protein by protease digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the IR protein that are detected and analyzed by mass spectrometry. Identification of a specific preferred subset of peptides for mass-spectrometric analysis is based on; 1) experimental determination of which peptide or peptides from a protein ionize in mass spectrometry analyses of Liquid Tissue™ lysates, and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

Protein lysates from cells procured directly from formalin (formaldehyde) fixed tissue were prepared using the Liquid Tissue™ reagents and protocol. This entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease such as trypsin. The skilled artisan will recognize that other proteases, and in particular, endoproteases may be used in place of, or in addition to, trypsin Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate may be employed. Ion trap mass spectrometers may, however, be the best type of mass spectrometer presently available for conducting global profiling of peptides. Although SRM/MRM assay can be developed and performed on any type of mass spectrometer, including a MALDI, ion trap, or triple quadrupole, an advantageous instrument platform for SRM/MRM assay is often considered to be a triple quadrupole instrument platform.

Once as many peptides as possible were identified in a single mass spectrometric analysis of a single lysate under the conditions employed, then that list of peptides was collated and used to determine the proteins that were detected in that lysate. That process was repeated for multiple Liquid Tissue™ lysates, and the very large list of peptides was collated into a single dataset. The resulting dataset represents the peptides that can be detected in the type of biological sample that was analyzed (after protease digestion), and specifically in a Liquid Tissue™ lysate of the biological sample, and thus includes the peptides for specific proteins, such as for example the IR protein.

In one embodiment, the IR tryptic peptides identified as useful in the determination of absolute or relative amounts of the IR protein, IR-A isoform and/or IR-B isoform, include either one or more, two or more, three or more, four or more, or all of the peptides of SEQ ID NO:1, SEQ ID NO:2, SEQ ID NO:3, SEQ ID NO:4, and SEQ ID NO:5, the sequences of each of which are shown in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, three or more, four or more of those peptides recited in Tables 1 and Table 2) are candidates for use in quantitative SRM/MRM assay for the IR protein, and IR-A and/or IR-B isoforms, in human biological samples, including directly in formalin fixed patient or subject tissue. Table 2 shows additional information regarding the peptides shown in Table 1.

TABLE 1

| SEQ ID | Peptide sequence |
|---|---|
| SEQ ID NO: 1 | TSSGTGAEDPRPSRK |
| SEQ ID NO: 2 | TFEDYLHNVVFVPRPSRK |
| SEQ ID NO: 3 | TFEDYLHNVVFVPRPSR |
| SEQ ID NO: 4 | TFEDYLHNVVFVPRK |
| SEQ ID NO: 5 | TFEDYLHNVVFVPR |

The IR peptides listed in Table 1 include those detected from multiple Liquid Tissue™ lysates of multiple different formalin fixed tissues of different human organs including prostate, colon, and breast. Each of those peptides is useful for quantitative SRM/MRM assay of the IR protein, and IR-A and/or IR-B isoforms, in formalin fixed tissue. Further data analysis of these experiments indicated no preference is observed for any specific peptides from any specific organ site. Thus, each of these peptides is believed to be suitable for conducting SRM/MRM assays of the IR protein, and IR-A and/or IR-B isoforms, on a Liquid Tissue™ lysate from any formalin fixed tissue originating from any biological sample or from any organ site in the body.

In one embodiment one or more peptides in Table 1, or any combination of those peptides (e.g., two or more, three or more, four or more, or all five) is assayed by a method that does not rely upon mass spectroscopy, including, but not limited to, immunological methods (e.g., Western blotting or ELISA). In one embodiment, the assays are conducted using formalin fixed tissue. Regardless of how information directed to the amount of the peptide(s) (absolute or relative) is obtained, the information may be employed in any of the methods described herein, including indicating (diagnosing) the presence of cancer in a patient or subject, determining the stage/grade/status of the cancer, providing a prognosis, or determining the therapeutics or treatment regimen for a patient or subject.

Embodiments of the present disclosure include compositions comprising one or more of the peptides in Tables 1 and/or 2, and may optionally include peptides that are isotopically labeled but otherwise identical to one or more of the peptides found in Tables 1 and/or 2. In some embodiments, the compositions comprise one or more, two or more, three or more, four or more, or all of the peptides in Tables 1 and/or 2, and may optionally include peptides, polypeptides, or proteins that comprise peptides that are isotopically labeled but otherwise identical to one or more of the peptides found in Table 1 and/or Table 2. Where peptides, polypeptides, or proteins that comprise the peptides in Tables 1 and/or 2 are employed, protease treatment releases peptides that are isotopically labeled but otherwise identical to the peptides in Tables 1 and/or 2. Each of the isotopically labeled peptides may be labeled with one or more isotopes selected independently from the group consisting of: $^{18}O$, $^{17}O$, $^{34}S$, $^{15}N$, $^{13}C$, $^{2}H$ or combinations thereof. Compositions comprising peptides from the IR protein, whether isotope labeled or not, do not need to contain all of the peptides from that protein (e.g., a complete set of tryptic peptides). In some embodiments the compositions do not contain all peptides in combination from IR, and particularly all of the peptides appearing in Table 1 and/or Table 2. Compositions comprising peptides may be in the form of dried or lyophilized materials, liquid (e.g., aqueous) solutions or suspensions, arrays, or blots.

TABLE 2

| SEQ ID | Peptide sequence | Mono Isotopic Mass | Precursor Charge State | Precursor m/z | Transition m/z | Ion Type |
|---|---|---|---|---|---|---|
| SEQ ID NO: 1 | TSSGTGAEDPRPSRK | 1544.74 | 2 | 773.384 | 390.245 | y3 |
| | | | 2 | 773.384 | 487.298 | y4 |
| | | | 2 | 773.384 | 643.399 | y5 |
| | | | 2 | 773.384 | 740.452 | y6 |
| | | | 2 | 773.384 | 855.479 | y7 |
| | | | 2 | 773.384 | 984.522 | y8 |
| | | | 2 | 773.384 | 1055.559 | y9 |
| | | | 2 | 773.384 | 1112.58 | y10 |
| | | | 2 | 773.384 | 1213.628 | y11 |
| | | | 2 | 773.384 | 1270.649 | y12 |
| | | | 2 | 773.384 | 1357.681 | y13 |
| SEQ ID NO: 2 | TFEDYLHNVVFVPRPSRK | 2203.14 | 2 | 1102.584 | 390.245 | y3 |
| | | | 2 | 1102.584 | 487.298 | y4 |
| | | | 2 | 1102.584 | 643.399 | y5 |
| | | | 2 | 1102.584 | 740.452 | y6 |
| | | | 2 | 1102.584 | 839.52 | y7 |
| | | | 2 | 1102.584 | 986.589 | y8 |
| | | | 2 | 1102.584 | 1085.657 | y9 |
| | | | 2 | 1102.584 | 1184.726 | y10 |
| | | | 2 | 1102.584 | 1298.769 | y11 |
| | | | 2 | 1102.584 | 1435.828 | y12 |
| SEQ ID NO: 3 | TFEDYLHNVVFVPRPSR | 2075.04 | 2 | 1038.537 | 359.203 | y3 |
| | | | 2 | 1038.537 | 515.304 | y4 |
| | | | 2 | 1038.537 | 612.357 | y5 |
| | | | 2 | 1038.537 | 711.426 | y6 |
| | | | 2 | 1038.537 | 858.494 | y7 |
| | | | 2 | 1038.537 | 957.562 | y8 |
| | | | 2 | 1038.537 | 1056.631 | y9 |
| | | | 2 | 1038.537 | 1170.674 | y10 |
| | | | 2 | 1038.537 | 1307.733 | y11 |
| | | | 2 | 1038.537 | 1420.817 | y12 |
| SEQ ID NO: 4 | TFEDYLHNVVFVPRK | 1862.95 | 2 | 932.491 | 400.266 | y3 |
| | | | 2 | 932.491 | 499.335 | y4 |
| | | | 2 | 932.491 | 646.403 | y5 |
| | | | 2 | 932.491 | 745.471 | y6 |
| | | | 2 | 932.491 | 844.54 | y7 |

TABLE 2-continued

| SEQ ID | Peptide sequence | Mono Isotopic Mass | Precursor Charge State | Precursor m/z | Ion Transition m/z | IonType |
|---|---|---|---|---|---|---|
| | | | 2 | 932.491 | 958.583 | y8 |
| | | | 2 | 932.491 | 1095.642 | y9 |
| | | | 2 | 932.491 | 1208.726 | y10 |
| | | | 2 | 932.491 | 1371.789 | y11 |
| | | | 2 | 932.491 | 1486.816 | y12 |
| SEQ ID NO: 5 | TFEDYLHNVVFV PR | 1734.86 | 2 | 868.444 | 371.24 | y3 |
| | | | 2 | 868.444 | 518.308 | y4 |
| | | | 2 | 868.444 | 617.376 | y5 |
| | | | 2 | 868.444 | 716.445 | y6 |
| | | | 2 | 868.444 | 830.488 | y7 |
| | | | 2 | 868.444 | 967.547 | y8 |
| | | | 2 | 868.444 | 1080.631 | y9 |
| | | | 2 | 868.444 | 1243.694 | y10 |
| | | | 2 | 868.444 | 1358.721 | y11 |
| | | | 2 | 868.444 | 1487.764 | y12 |

One consideration for conducting an SRM/MRM assay is the type of instrument that may be employed in the analysis of the peptides. Although SRM/MRM assays can be developed and performed on any type of mass spectrometer, including a MALDI, ion trap, or triple quadrupole, the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement SRM/MRM assay for each peptide derived from the IR protein it is desirable to utilize information in addition to the peptide sequence in the analysis. That additional information may be used in directing and instructing the mass spectrometer (e.g. a triple quadrupole mass spectrometer) to perform the correct and focused analysis of specific targeted peptide(s) such that the assay may be effectively performed.

The additional information about target peptides in general, and about specific IR peptides, may include one or more of the mono isotopic mass of each peptide, its precursor charge state, the precursor m/z value, the m/z transition ions, and the ion type of each transition ion. Additional peptide information that may be used to develop an SRM/MRM assay for the IR protein, and IR-A and/or IR-B isoforms, is shown in Table 2 for the five (5) IR peptides from the list in Table 1. Similar additional information described for the peptides shown in Table 2 may be prepared, obtained, and applied to the analysis of the other peptides from the IR protein, including those produced by the action of other proteases or combinations of proteases (e.g., trypsin and/or Lys C).

In one embodiment, the additional information about specific IR peptides, includes one or more, two or more, or three or more of the mono isotopic mass of each peptide, its precursor charge state, the precursor m/z value, the m/z transition ions, and the ion type of each transition ion for peptides resulting from Lys C proteolysis of IR proteins, including either one or both of the IR-A and/or IR-B isoforms.

In another embodiment, the additional information about specific IR peptides, includes one or more, two or more, or three or more of the mono isotopic mass of each peptide, its precursor charge state, the precursor m/z value, the m/z transition ions, and the ion type of each transition ion for peptides resulting from trypsin proteolysis of IR proteins, including either one or both of the IR-A and/or IR-B isoforms.

In still another embodiment, the additional information about specific IR peptides, includes one or more, two or more, or three or more of the mono isotopic mass of each peptide, its precursor charge state, the precursor m/z value, the m/z transition ions, and the ion type of each transition ion for peptides resulting from trypsin and Lys C proteolysis of IR proteins, including either one or both of the IR-A and/or IR-B isoforms.

The method described below was used to: 1) identify candidate peptides from the IR protein that can be used for a mass spectrometry-based SRM/MRM assay for the IR protein, and the IR-A and/or IR-B isoforms, 2) develop individual SRM/MRM assay, or assays, for target peptides from the IR protein and 3) apply quantitative assays to cancer diagnosis and/or choice of optimal therapy.

Assay Method

1. Identification of SRM/MRM Candidate Fragment Peptides for the IR Protein
   a. Prepare a Liquid Tissue™ protein lysate from a formalin fixed biological sample using a protease or proteases, (that may or may not include trypsin), to digest proteins
   b. Analyze all protein fragments in the Liquid Tissue™ lysate on an ion trap tandem mass spectrometer and identify all fragment peptides from the IR protein, where individual fragment peptides do not contain any peptide modifications such as phosphorylations or glycosylations c. Analyze all protein fragments in the Liquid Tissue™ lysate on an ion trap tandem mass spectrometer and identify all fragment peptides from the IR protein that carry peptide modifications such as for example phosphorylated or glycosylated residues d. All peptides generated by a specific digestion method from the entire, full length IR protein potentially can be measured, but preferred peptides used for development of the SRM/MRM assay are those that are identified by mass spectrometry directly in a complex Liquid Tissue™ protein lysate prepared from a formalin fixed biological sample e. Peptides that are specifically modified (phosphorylated, glycosylated, etc.) in a patient or subject tissue and which ionize, and thus can be detected, in a mass spectrometer when analyzing a Liquid Tissue™ lysate from a formalin fixed biological sample are identified as candidate peptides for assaying peptide modifications of the IR protein 2. Mass Spectrometry Assay for Fragment Peptides from IR Protein a. SRM/MRM assay on a triple quadrupole mass spectrometer for individual fragment peptides identified in a Liquid Tissue™ lysate is applied to peptides from the IR protein i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.

iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer b. Perform SRM/MRM analysis so that the amount of the fragment peptide of the IR protein that is detected, as a function of the unique SRM/MRM signature peak area from an SRM/MRM mass spectrometry analysis, can indicate both the relative and absolute amount of the protein in a particular protein lysate.

i. Relative quantitation may be achieved by:

1. Determining increased or decreased presence of the IR protein by comparing the SRM/MRM signature peak area from a given IR peptide detected in a Liquid Tissue™ lysate from one formalin fixed biological sample to the same SRM/MRM signature peak area of the same IR fragment peptide in at least a second, third, fourth or more Liquid Tissue™ lysates from least a second, third, fourth or more formalin fixed biological samples 2. Determining increased or decreased presence of the IR protein by comparing the SRM/MRM signature peak area from a given IR peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.

3. Determining increased or decreased presence of the IR protein, IR-A and/or IR-B isoforms, by comparing the SRM/MRM signature peak area for a given IR peptide to the SRM/MRM signature peak areas from other fragment peptides derived from different proteins within the same Liquid Tissue™ lysate from the formalin fixed biological sample in order to normalize changing levels of IR protein, and IR-A and/or IR-B isoforms, to levels of other proteins that do not change their levels of expression under various cellular conditions.

4. These assays can be applied to both unmodified fragment peptides and for modified fragment peptides of the IR protein, where the modifications include but are not limited to phosphorylation and/or glycosylation, and where the relative levels of modified peptides are determined in the same manner as determining relative amounts of unmodified peptides.

ii. Absolute quantitation of a given peptide may be achieved by comparing the SRM/MRM signature peak area for a given fragment peptide from the IR protein in an individual biological sample to the SRM/MRM signature peak area of an internal fragment peptide standard spiked into the protein lysate from the biological sample 1. The internal standard is a labeled synthetic version of the fragment peptide from the IR protein that is being interrogated. This standard is spiked into a sample in known amounts, and the SRM/MRM signature peak area can be determined for both the internal fragment peptide standard and the native fragment peptide in the biological sample separately, followed by comparison of both peak areas 2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.

3. Apply Fragment Peptide Quantitation to Cancer Diagnosis and Treatment a. Perform relative and/or absolute quantitation of fragment peptide levels of the IR protein, and IR-A and/or IR-B isoforms, and demonstrate that the previously-determined association, as well understood in the field of cancer, of IR protein, and IR-A and/or IR-B isoforms, expression to the stage/grade/status of cancer in patient or subject tumor tissue is confirmed b. Perform relative and/or absolute quantitation of fragment peptide levels of the IR, and IR-A and/or IR-B isoforms, protein and demonstrate correlation with clinical outcomes from different treatment strategies, wherein this correlation has already been demonstrated in the field or can be demonstrated in the future through correlation studies across cohorts of patients or subjects and tissue from those patients or subjects. Once either previously established correlations or correlations derived in the future are confirmed by this assay then the assay method can be used to determine optimal treatment strategy A Mass Spectrometry Assay for Fragment Peptides from IR Protein a. SRM/MRM assay to determine the amount of the fragment peptide of the IR protein that is detected to determine the relative and/or absolute amount of the IR-A and/or IR-B protein(s) in a protein lysate.
  i. Relative quantitation may be achieved by:
    1. Determining increased or decreased presence of the IR protein by comparing the SRM/MRM signature peak area from a given IR peptide detected in a Liquid Tissue™ lysate from one formalin fixed biological sample to the same SRM/MRM signature peak area of the same IR fragment peptide in at least a second, third, fourth or more Liquid Tissue™ lysates from least a second, third, fourth or more formalin fixed biological samples
    2. Determining increased or decreased presence of the IR protein by comparing the SRM/MRM signature peak area from a given IR peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
    3. Determining increased or decreased presence of the IR protein, IR-A isoform and/or IR-B isoform, by comparing the SRM/MRM signature peak area for a given IR peptide to the SRM/MRM signature peak areas from other fragment peptides derived from different proteins within the same Liquid Tissue™ lysate from the formalin fixed biological sample in order to normalize changing levels of IR protein, IR-A isoform and/or IR-B isoform, to levels of other proteins that do not change their levels of expression under various cellular conditions.
    4. These assays can be applied to both unmodified fragment peptides and for modified fragment peptides of the IR protein, where the modifications include but are not limited to phosphorylation and/or glycosylation, and where the relative levels of modified peptides are determined in the same manner as determining relative amounts of unmodified peptides.
  ii. Absolute quantitation of a given peptide or the protein it is derived from may be achieved by comparing the SRM/MRM signature peak area for a given fragment peptide from the IR protein in an individual biological sample to the SRM/MRM signature peak area of an internal fragment peptide standard spiked into the protein lysate from the biological sample.

The internal standard is a labeled synthetic version of the fragment peptide from the IR protein that is being interrogated (or a protein or polypeptide comprising the labeled synthetic version of the fragment peptide that is released upon proteolysis). The standard is spiked into a sample in known amounts, and the SRM/MRM signature peak area can be determined for both the internal fragment peptide standard and the native fragment peptide in the biological sample separately, followed by comparison of both peak areas.

This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.

Assessment of IR protein, IR-A isoform and/or IR-B isoform, levels in tissues based on analysis of formalin fixed patient-derived or subject-derived tissue can provide diagnostic, prognostic, and therapeutically-relevant information about each particular patient or subject. In one embodiment, this disclosure describes a method for measuring the level of the IR protein, IR-A isoform and/or IR-B isoform, in a biological sample, comprising detecting and/or quantifying the amount of one or more modified or unmodified IR fragment peptides in a protein digest prepared from said biological sample using mass spectrometry; and calculating the level of modified or unmodified IR protein, IR-A isoform and/or IR-B isoform, in said sample; and wherein said level is a relative level or an absolute level. In a related embodiment, quantifying one or more IR fragment peptides comprises determining the amount of the each of the IR fragment peptides in a biological sample by comparison to an added internal standard peptide of known amount, wherein each of the IR fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring the level of the IR protein, and/or IR-A and/or IR-B isoforms, in a biological sample described herein (or fragment peptides as surrogates thereof) may be used as a diagnostic indicator of cancer in a patient or subject. In one embodiment, the results from measurements of the level of the IR protein, and/or IR-A and/or IR-B isoforms, may be employed to determine the diagnostic stage/grade/status of a cancer by correlating (e.g., comparing) the level of IR protein, and/or IR-A and/or IR-B isoforms, found in a tissue with the level of that protein found in normal and/or cancerous or precancerous tissues.

Because both nucleic acids and protein can be analyzed from the same Liquid Tissue biomolecular preparation it is possible to generate additional information about disease diagnosis and drug treatment decisions from the same sample. For example, the IR protein is a tyrosine kinase receptor that is capable of stimulating uncontrolled cell growth (cancer) by activation of specific cell signal protein pathways. If IR is expressed by certain cells at increased levels, when assayed by SRM the data can provide information about the state of the cells and their potential for uncontrolled growth, potential drug resistance and the development of cancers can be obtained. At the same time, information about the status of the IR gene and/or the nucleic acids and proteins it encodes (e.g., mRNA molecules and their expression levels or splice variations, particularly those leading to the IR-A and I-B isoforms) can be obtained from nucleic acids present in the same biomolecular preparation. For example information about IR and/or its isoforms, and/or one, two, three, four or more additional proteins may be assessed by examining the nucleic acids encoding those proteins. Those nucleic acids can be examined, for example, by one or more. two or more, or three or more of: sequencing methods, conducting restriction fragment polymorphism analysis, identification of deletions, insertions, and/or determining the presence of mutations, including but not limited to, single base pair polymorphisms, transitions and/or transversions.

The above description and exemplary embodiments of methods and compositions are illustrative of the scope of the present disclosure. Because of variations which will be apparent to those skilled in the art, however, the present disclosure is not intended to be limited to the particular embodiments described above.

---

---

The invention claimed is:

1. A method for measuring the level of the Insulin Receptor (IR) protein, and/or its isoforms, IR-A and/or IR-B, in a human biological sample of formalin-fixed tissue, comprising detecting and/or quantifying the amount of one or more IR fragment peptides in a protein digest prepared from said human biological sample using mass spectrometry wherein the IR fragment peptides are selected from the group consisting of the peptides of SEQ ID NO:3 and SEQ ID NO:5; and calculating the level of IR, IR-A isoform and/or IR-B isoform, protein in said sample;

wherein said amount is a relative amount or an absolute amount.

2. The method of claim 1, further comprising the step of fractionating said protein digest prior to detecting and/or quantifying the amount of said one or more IR fragment peptides.

3. The method of claim 2, wherein said fractionating step is selected from the group consisting of gel electrophoresis, liquid chromatography, capillary electrophoresis, nano-reversed phase liquid chromatography, high performance liquid chromatography, or reverse phase high performance liquid chromatography.

4. The method of claim 1, wherein said mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.

5. The method of claim 4, wherein the mode of mass spectrometry used is Selected Reaction Monitoring (SRM), Multiple Reaction Monitoring (MRM), and/or multiple Selected Reaction Monitoring (mSRM), or any combination thereof.

6. The method of 1, wherein the tissue is paraffin embedded tissue.

7. The method of claim 1, wherein the tissue is obtained from a tumor.

8. The method of claim 1, comprising quantifying an IR fragment peptide.

9. The method of claim 8, wherein quantifying the IR fragment peptide comprises comparing an amount of said one or more IR fragment peptides in one biological sample to the amount of the same IR fragment peptide or peptides in a different and separate biological sample.

10. The method of claim 9, wherein quantifying one or more IR fragment peptides comprises determining the amount of each of the IR fragment peptides in a biological sample by comparison to an added internal standard peptide of known amount, wherein each of the IR fragment peptides in the biological sample is compared to an internal standard peptide having the same amino acid sequence, and wherein the internal standard peptide is an isotopically labeled peptide.

11. The method of claim 10, wherein the isotopically labeled internal standard peptide comprises one or more heavy stable isotopes selected from $^{18}O$, $^{17}O$, $^{34}S$, $^{15}N$, $^{13}C$, $^{2}H$ or combinations thereof.

12. The method of claim 1, wherein detecting and/or quantifying the amount of one or more IR fragment peptides in the protein digest indicates the presence of IR protein, IR-A and/or IR-B, and an association with cancer in a patient or subject.

13. The method of claim 12, further comprising correlating the results of said detecting and/or quantifying the amount of one or more IR fragment peptides, or the amount of said IR protein, IR-A isoform and/or IR-B isoform, to the diagnostic stage/grade/status of the cancer.

14. The method of claim 13, wherein correlating the results of said detecting and/or quantifying the amount of one or more IR fragment peptides, or the amount of said IR protein, IR-A isoform and/or IR-B isoform, to the diagnostic stage/grade/status of the cancer is combined with detecting and/or quantifying the amount of other proteins or peptides from other proteins in a multiplex format to provide additional information about the diagnostic stage/grade/status of the cancer.

15. The method of claim 1, further comprising selecting for a patient or subject from which said biological sample was obtained a treatment based on the presence, absence, or amount of one or more IR fragment peptides or the amount of IR protein, IR-A isoform and/or IR-B isoform.

16. The method of claim 1, further comprising administering to a patient or subject from which said biological sample was obtained a therapeutically effective amount of a therapeutic agent, wherein the therapeutic agent and/or amount of the therapeutic agent administered is based upon amount of one or more IR fragment peptides or the amount of IR protein, IR-A isoform and/or IR-B isoform.

17. The method of claim 15, wherein the treatment or the therapeutic agent is directed to cancer cells expressing IR protein, IR-A isoform and/or IR-B isoform.

18. The method of claim 1, wherein said protein digest comprises a protease digest.

* * * * *

SEQUENCE LISTING

```
<160> NUMBER OF SEQ ID NOS: 5

<210> SEQ ID NO 1
<211> LENGTH: 15
<212> TYPE: PRT
<213> ORGANISM: Homo sapiens

<400> SEQUENCE: 1

Thr Ser Ser Gly Thr Gly Ala Glu Asp Pro Arg Pro Ser Arg Lys
1               5                   10                  15

<210> SEQ ID NO 2
<211> LENGTH: 18
<212> TYPE: PRT
<213> ORGANISM: Homo sapiens

<400> SEQUENCE: 2

Thr Phe Glu Asp Tyr Leu His Asn Val Val Phe Val Pro Arg Pro Ser
1               5                   10                  15

Arg Lys

<210> SEQ ID NO 3
<211> LENGTH: 17
<212> TYPE: PRT
<213> ORGANISM: Homo sapiens

<400> SEQUENCE: 3

Thr Phe Glu Asp Tyr Leu His Asn Val Val Phe Val Pro Arg Pro Ser
1               5                   10                  15

Arg

<210> SEQ ID NO 4
<211> LENGTH: 15
<212> TYPE: PRT
<213> ORGANISM: Homo sapiens

<400> SEQUENCE: 4

Thr Phe Glu Asp Tyr Leu His Asn Val Val Phe Val Pro Arg Lys
1               5                   10                  15

<210> SEQ ID NO 5
<211> LENGTH: 14
<212> TYPE: PRT
<213> ORGANISM: Homo sapiens

<400> SEQUENCE: 5

Thr Phe Glu Asp Tyr Leu His Asn Val Val Phe Val Pro Arg
1               5                   10
```